United States Patent
Wall

(10) Patent No.: US 11,617,603 B2
(45) Date of Patent: Apr. 4, 2023

(54) MODULAR SURGICAL INSTRUMENT SYSTEM WITH RATCHETING REDUCTION MECHANISM

(71) Applicant: Warsaw Orthopedic, Inc., Warsaw, IN (US)

(72) Inventor: Daniel P. Wall, Cordova, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 231 days.

(21) Appl. No.: 17/116,215

(22) Filed: Dec. 9, 2020

(65) Prior Publication Data
US 2022/0175425 A1     Jun. 9, 2022

(51) Int. Cl.
| | | |
|---|---|---|
| A61B 17/70 | (2006.01) | |
| A61B 17/88 | (2006.01) | |
| A61B 17/00 | (2006.01) | |

(52) U.S. Cl.
CPC ...... *A61B 17/7082* (2013.01); *A61B 17/8891* (2013.01); *A61B 2017/00407* (2013.01)

(58) Field of Classification Search
CPC ............ A61B 17/7086; A61B 17/7077; A61B 17/7079; A61B 17/708; A61B 17/7076; A61B 17/7082; A61B 17/7083; A61B 17/7085; A61B 17/7091; A61B 17/783; A61B 17/7089
See application file for complete search history.

(56) References Cited

U.S. PATENT DOCUMENTS

| | | |
|---|---|---|
| 7,618,424 B2 | 11/2009 | Wilcox et al. |
| 7,794,464 B2 | 9/2010 | Bridwell et al. |
| 7,811,288 B2 | 10/2010 | Jones et al. |
| 8,147,524 B2 | 4/2012 | Piza Vallespir |
| 8,162,952 B2 | 4/2012 | Cohen et al. |
| 8,192,440 B2 | 6/2012 | Jones et al. |
| 8,211,110 B1 | 7/2012 | Corin et al. |
| 8,221,474 B2 | 7/2012 | Bridwell et al. |
| 8,277,453 B2 | 10/2012 | Kave et al. |
| 8,394,109 B2 | 3/2013 | Hutton et al. |
| 8,475,467 B2 | 7/2013 | Manninen |
| 8,491,590 B2 | 7/2013 | Stad et al. |
| 8,500,741 B2 | 8/2013 | Hansen |
| 8,608,746 B2 | 12/2013 | Kolb et al. |
| 8,608,782 B1 | 12/2013 | Rovner |
| 8,623,022 B2 | 1/2014 | Forton et al. |
| 8,636,743 B2 | 1/2014 | Jones et al. |
| 8,672,944 B2 | 3/2014 | Boachie-Adjei et al. |

(Continued)

*Primary Examiner* — Jan Christopher L Merene
*Assistant Examiner* — Allie D Cline
(74) *Attorney, Agent, or Firm* — Fox Rothschild LLP

(57) ABSTRACT

A modular surgical instrument is provided that includes a tower having a first end, a second end and a ratchet segment between the first end and the second end. The instrument includes a ratchet reduction mechanism. The ratchet reduction mechanism includes a ratchet lever, a linear ratchet rack integrated into a ratchet segment of the tower at a location between the first end and the second end, and a ratchet collar coupled to the ratchet lever. The ratchet collar is configured to slide along the ratchet segment by application of an applied force. The instrument includes a reducer that may be affixed to the ratchet reduction mechanism. The reducer is configured to move in unison with the slide of the ratchet collar.

17 Claims, 9 Drawing Sheets

(56) References Cited

U.S. PATENT DOCUMENTS

| | | | |
|---|---|---|---|
| 8,702,713 B2 | 4/2014 | Nayet et al. | |
| 8,821,502 B2 | 9/2014 | Gleeson et al. | |
| 8,894,655 B2 | 11/2014 | Fallin et al. | |
| 8,900,248 B2 | 12/2014 | Biyani | |
| 8,906,034 B2 | 12/2014 | Gleeson et al. | |
| 8,951,257 B2 | 2/2015 | Lenke et al. | |
| 8,956,360 B2 | 2/2015 | Boachie-Adjei et al. | |
| 8,979,851 B2 | 3/2015 | Fallin et al. | |
| 9,005,204 B2 | 4/2015 | Manninen et al. | |
| 9,011,447 B2 | 4/2015 | Arnett et al. | |
| 9,060,825 B2 | 6/2015 | Hutton et al. | |
| 9,066,762 B2 | 6/2015 | Jones et al. | |
| 9,101,412 B2 | 8/2015 | Bootwala et al. | |
| 9,119,684 B2 | 9/2015 | Fallin et al. | |
| 9,131,967 B2 | 9/2015 | Stad et al. | |
| 9,155,573 B2 | 10/2015 | May et al. | |
| 9,179,957 B2 | 11/2015 | Ibrahim et al. | |
| 9,198,692 B1 | 12/2015 | Doose et al. | |
| 9,220,539 B2 | 12/2015 | McBride et al. | |
| 9,241,742 B2 | 1/2016 | Stad | |
| 9,247,977 B2 | 2/2016 | Fallin et al. | |
| 9,254,152 B2 | 2/2016 | Manninen | |
| 9,259,245 B2 | 2/2016 | Maruenda Paulino et al. | |
| 9,289,248 B2 | 3/2016 | Seex et al. | |
| 9,289,251 B2 | 3/2016 | Leroux et al. | |
| 9,308,030 B2 | 4/2016 | Manninen | |
| 9,314,273 B2 | 4/2016 | Iott et al. | |
| 9,314,280 B2 | 4/2016 | Corin | |
| 9,326,798 B2 | 5/2016 | Kolb et al. | |
| 9,402,660 B2 | 8/2016 | Brinkman et al. | |
| 9,414,860 B2 | 8/2016 | Boachie-Adjei et al. | |
| 9,468,476 B2 | 10/2016 | Boachie-Adjei et al. | |
| 9,480,500 B2 | 11/2016 | Ibrahim et al. | |
| 9,480,504 B1 | 11/2016 | Schafer et al. | |
| 9,561,062 B2 | 2/2017 | Hayes et al. | |
| 9,579,140 B2 | 2/2017 | Jones et al. | |
| 9,655,685 B2 | 5/2017 | Fallin et al. | |
| 9,668,776 B2 | 6/2017 | Ibrahim et al. | |
| 9,681,899 B2 | 6/2017 | Artaki et al. | |
| 9,693,806 B2 | 7/2017 | Manninen et al. | |
| 9,808,295 B2 | 11/2017 | Peukert et al. | |
| 9,861,393 B2 | 1/2018 | Ibrahim et al. | |
| 9,877,750 B2 | 1/2018 | Iott et al. | |
| 9,888,945 B2 | 2/2018 | Walters et al. | |
| 9,907,582 B1 | 3/2018 | Olea | |
| 9,974,577 B1 | 5/2018 | Smith et al. | |
| 10,028,771 B2 | 7/2018 | Artaki et al. | |
| 10,028,773 B2 | 7/2018 | Ibrahim et al. | |
| 10,028,774 B2 | 7/2018 | Meyer | |
| 10,034,695 B1 | 7/2018 | Schafer et al. | |
| 10,070,900 B2 | 9/2018 | Hayes et al. | |
| 10,070,936 B2 | 9/2018 | Fallin et al. | |
| 10,085,807 B2 | 10/2018 | Butters et al. | |
| 10,098,665 B2 | 10/2018 | Rutschmann et al. | |
| 10,111,650 B2 | 10/2018 | Nel | |
| 10,136,927 B1* | 11/2018 | Lish | A61B 17/7086 606/86 |
| 10,213,232 B2 | 2/2019 | Ibrahim et al. | |
| 10,390,862 B2 | 8/2019 | Bobbitt et al. | |
| 10,426,538 B2 | 10/2019 | Jones et al. | |
| 10,617,449 B2 | 4/2020 | Corbin et al. | |
| 10,682,166 B2 | 6/2020 | Smith et al. | |
| 10,687,867 B2 | 6/2020 | Artaki et al. | |
| 10,687,868 B2 | 6/2020 | Heuer | |
| 10,709,477 B2 | 7/2020 | Manninen et al. | |
| 10,716,600 B1 | 7/2020 | Olea et al. | |
| 10,716,601 B2 | 7/2020 | Schafer et al. | |
| 10,765,488 B2 | 9/2020 | Fallin et al. | |
| 10,772,662 B2 | 9/2020 | Rezach | |
| 2005/0006896 A1* | 1/2005 | Naito | F16L 37/133 285/322 |
| 2005/0021040 A1 | 1/2005 | Bertagnoli | |
| 2008/0077155 A1 | 3/2008 | Diederich et al. | |
| 2008/0172062 A1 | 7/2008 | Donahue et al. | |
| 2009/0228054 A1* | 9/2009 | Hoffman | A61B 17/7086 606/86 A |
| 2010/0305625 A1* | 12/2010 | Kuntz | A61B 17/7076 606/86 R |
| 2011/0098537 A1 | 4/2011 | Justis et al. | |
| 2011/0257692 A1* | 10/2011 | Sandstrom | A61B 17/7085 606/86 A |
| 2012/0203279 A1 | 8/2012 | Walters et al. | |
| 2014/0107707 A1 | 4/2014 | Rovner | |
| 2015/0335359 A1 | 11/2015 | May et al. | |
| 2016/0030093 A1* | 2/2016 | Walker | A61B 17/7032 606/86 A |
| 2016/0089188 A1* | 3/2016 | McBride, Jr. | A61B 17/7085 606/279 |
| 2017/0020583 A1 | 1/2017 | Tsai et al. | |
| 2018/0153593 A1* | 6/2018 | Goel | A61B 17/7032 606/86 |
| 2019/0090908 A1 | 3/2019 | Stad | |
| 2019/0142475 A1 | 5/2019 | Ibrahim et al. | |
| 2019/0231394 A1 | 8/2019 | Bechtel et al. | |
| 2019/0274740 A1* | 9/2019 | Stoll | A61B 17/7086 606/86 |
| 2020/0054361 A1 | 2/2020 | Peultier et al. | |
| 2020/0107862 A1 | 4/2020 | Biedermann et al. | |
| 2020/0179008 A1 | 6/2020 | Biedermann et al. | |
| 2020/0237410 A1 | 7/2020 | Gabos et al. | |
| 2020/0297393 A1 | 9/2020 | Olea et al. | |
| 2020/0297394 A1 | 9/2020 | Schafer et al. | |
| 2020/0305932 A1 | 10/2020 | Park | |

\* cited by examiner

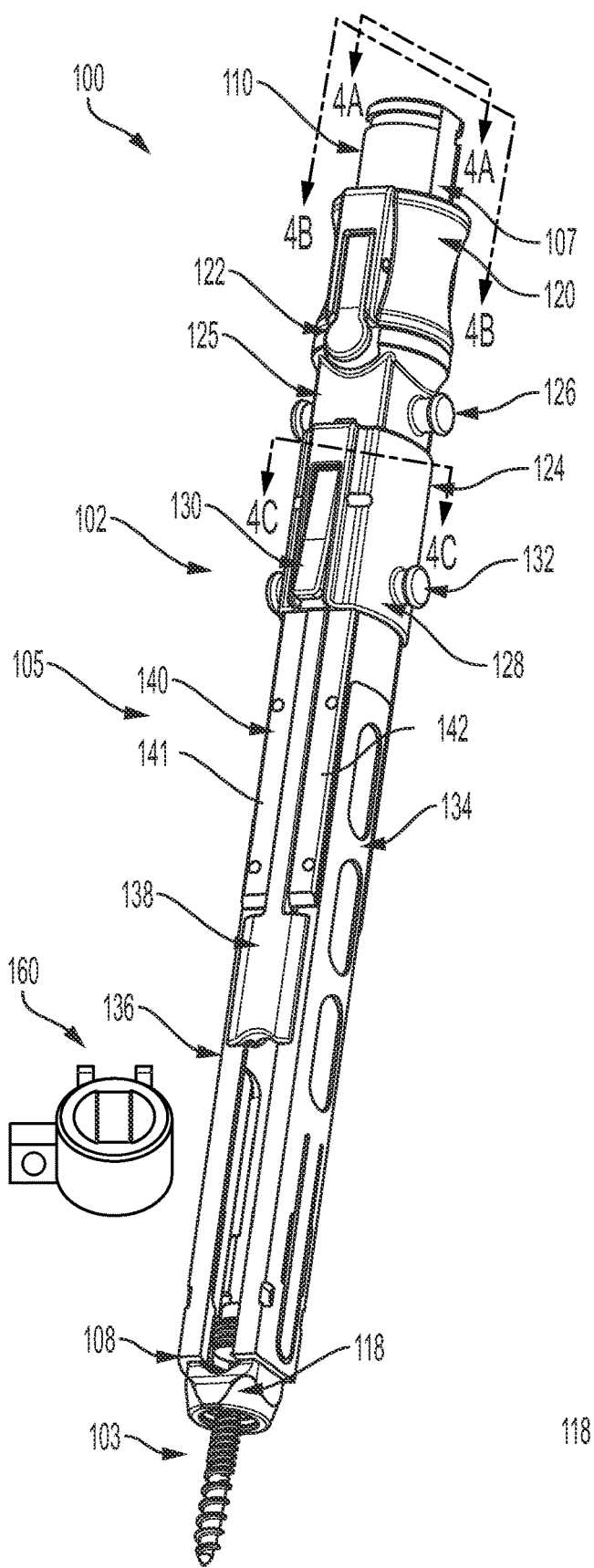
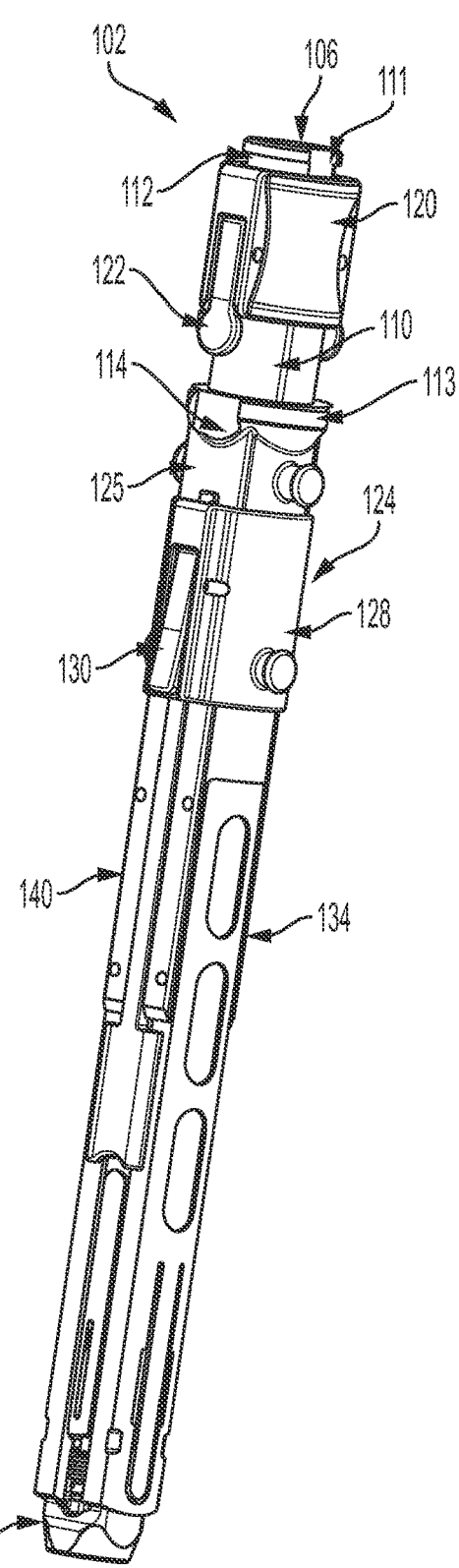
FIG. 1A
FIG. 1B

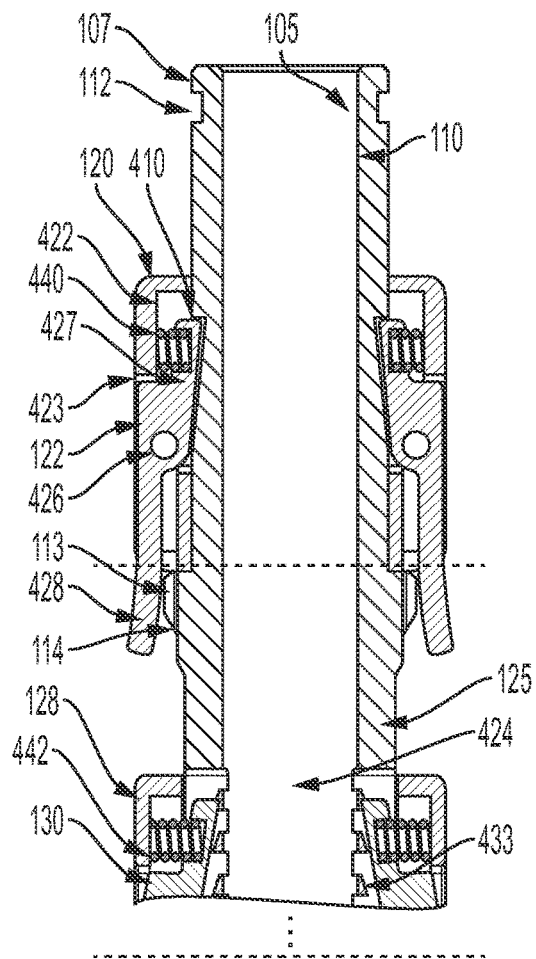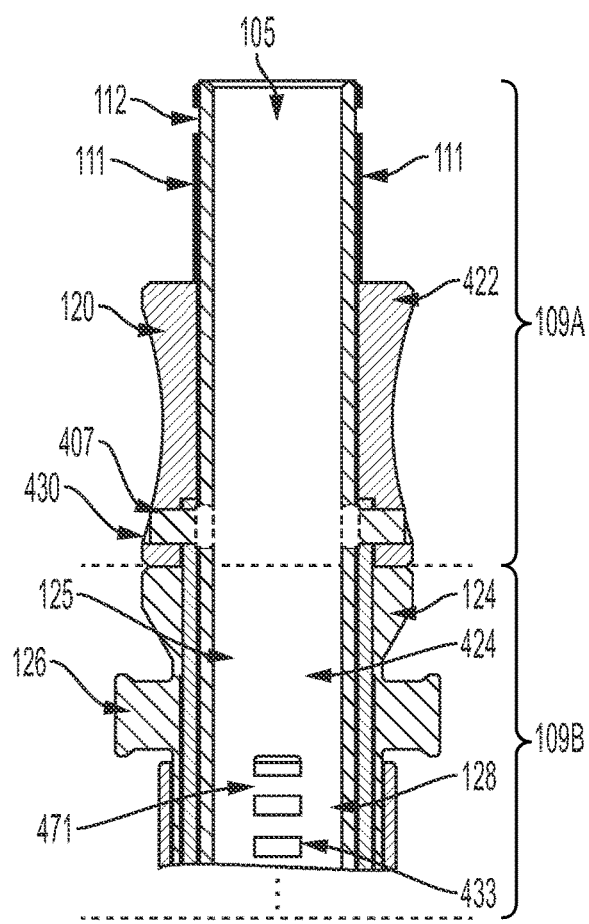
FIG. 4A
FIG. 4B
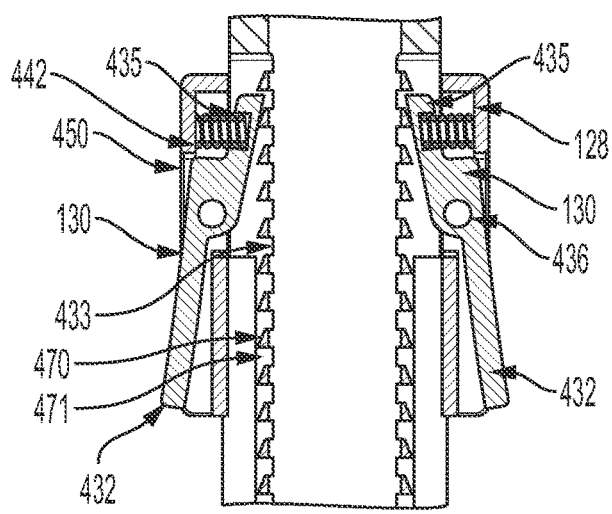
FIG. 4C

MODULAR SURGICAL INSTRUMENT SYSTEM WITH RATCHETING REDUCTION MECHANISM

FIELD

The present technology is generally related to a modular surgical instrument system that may be used for various tasks depending upon the module to incorporate into the instrument, such as, connecting portions of a screw system, for locking the head on a screw, connections for rod reduction or connections for various other uses such as attachments for auxiliary tools.

BACKGROUND

Spinal disorders such as scoliosis and other curvature abnormalities, may cause degenerative conditions over time and deformity. The degenerative conditions and deformities of the spine may result in symptoms, such as without limitation, nerve damage, and partial or complete loss of mobility and chronic pain.

Treatment options are limited based on the severity of the spinal disorder. While, non-surgical treatments, such as rehabilitation and exercise can be effective, these treatments may fail to relieve the symptoms associated with spinal disorders. Thus, medication may be needed to relieve pain or to address other symptoms.

Surgical treatment of these spinal disorders includes correction, fusion, fixation, discectomy, laminectomy and implantable prosthetics, for example. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior art technologies.

SUMMARY

The techniques of this disclosure generally relate to a system with a modular surgical instrument having an integrated reducer and a universal handle interface to allow different interchangeable surgical auxiliary tools to be affixed during surgery while the reducer is deployed.

In one aspect, the present disclosure provides a modular surgical instrument that includes a tower having a first end, a second end and a ratchet segment between the first end and the second end. The instrument includes a ratchet reduction mechanism. The ratchet reduction mechanism includes a ratchet lever, a linear ratchet rack integrated into a ratchet segment of the tower at a location between the first end and the second end, and a ratchet collar coupled to the ratchet lever. The ratchet collar is configured to slide along the ratchet segment by application of an applied force. The instrument includes a reducer affixed to the ratchet reduction mechanism. The reducer is configured to move in unison with the slide of the ratchet collar.

In another aspect, the disclosure provides a surgical implant system that includes a polyaxial head and a modular surgical instrument. The instrument includes a tower having a first end, a second end and a ratchet segment between the first end and the second end. The instrument includes a ratchet reduction mechanism that includes a ratchet collar interfaced with the ratchet segment. The instrument includes a reducer affixed to the ratchet reduction mechanism and is configured to move in unison with sliding motion of the ratchet collar toward the polyaxial head.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 1A is a perspective view that illustrates components of a modular surgical implant system with principles of the present disclosure.

FIG. 1B is a perspective view that illustrates the modular surgical instrument of FIG. 1A with a locking mechanism in an unlocked position.

FIG. 4A is partial a cross-sectional view along cross section 4A-4A that illustrates an upper end portion of a tower of modular surgical instrument of FIG. 1A.

FIG. 4B is partial a cross-sectional view along cross section 4B-4B that illustrates an upper end portion of a tower of modular surgical instrument of FIG. 1A.

FIG. 4C is partial a cross-sectional view along cross section 4C-4C that illustrates an upper end portion of a tower of modular surgical instrument of FIG. 1A.

DETAILED DESCRIPTION

Figure 2:
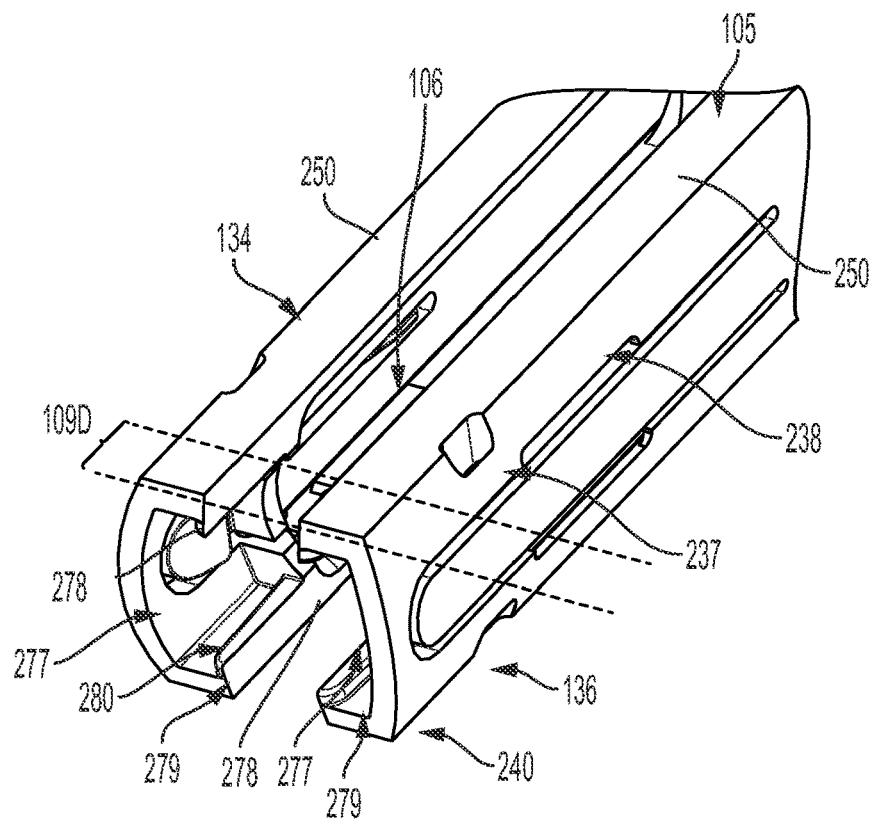
FIG. 2 is a perspective view that illustrates a lower end portion of a tower of modular surgical instrument of FIG. 1A.

The embodiments of a modular surgical implant system are discussed in terms of medical devices for the treatment of musculoskeletal disorders and more particularly, in terms of a surgical system and a method for treating a spine. In some embodiments, the system includes a modular surgical instrument and interchangeable surgical auxiliary tools mated to the modular surgical instrument and related methods of use that can be employed with spinal constructs including bone fasteners and connectors that provide a universal connection system for spine surgeons. In some embodiments, the modular surgical implant system incorporates a reducer into the instrument's tower thereby minimizing inventory while creating assemblies customized for a specific patient. In some embodiments, the modular surgical implant system incorporates a universal connector to connect one or more tools or accessories to the tower that may be interchanged during surgery and while the reducer is deployed.

The disclosure is directed, for example, to surgical tools used to treat spinal disorders such as, for example, degenerative disc disease, disc herniation, osteoporosis, spondylolisthesis, stenosis, scoliosis and other curvature abnormalities, kyphosis, tumor and fractures.

The system of the present disclosure may be understood more readily by reference to the following detailed description of the embodiments taken in connection with the accompanying drawing figures that form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, front, back, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical implant system including a modular surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures.

Turning to FIG. 1A, a perspective view of components of a modular surgical implant system 100 with principles of the present disclosure is illustrated. FIG. 1B is a perspective view of the modular surgical instrument 102 of FIG. 1A with a locking mechanism in an unlocked position.

The components of the system 100 can be fabricated from biologically acceptable materials suitable for medical applications, including metals, synthetic polymers, ceramics and bone material and/or their composites. For example, the components of system 100, individually or collectively, can be fabricated from materials such as stainless steel alloys, aluminum, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologic Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of the system 100 may have material composites, including the above materials, to achieve various desired characteristics such as strength, rigidity, elasticity, compliance, biomechanical performance, durability and radiolucency or imaging preference. The components of the system 100, individually or collectively, may also be fabricated from a heterogeneous material such as a combination of two or more of the above-described materials. The components of the system 100 may be monolithically formed, integrally connected or include fastening elements and/or instruments, as described herein.

The system 100 may include at least one surgical instrument and is employed, for example, with an open or mini-open, minimal access and/or minimally invasive including percutaneous surgical technique to deliver and fasten an implant at a surgical site within a body of a patient, for example, a section of a spine. In one embodiment, the components of the system 100 are configured to fix a bone fastener, such as a pedicle screw, with tissue for a surgical treatment to treat various spine pathologies, such as those described herein.

It is contemplated that the present disclosure may be employed with other osteal and bone related applications, including those associated with diagnostics and therapeutics. It is further contemplated that the disclosed surgical system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the thoracic, lumbar, sacral, cervical, and pelvic sections of the spinal column. The system 100 of the present disclosure may also be used on animals, simulated spinal bone models or other non-living substrates, such as, without limitations for use in testing and training.

Referring still to FIG. 1A, the modular surgical implant system 100 may include a modular surgical instrument 102. The modular surgical instrument 102 may be used for reduction, set screw delivery, counter torque, derotation, head insertion and head locking. The system 100 may include a bone fastener 103 (i.e., pedicle screw) adapted to be attached to a lower (second) end of the modular surgical instrument 102 and a second auxiliary tool fastening mechanism 160 adapted to be attached to an upper (first) end of the modular surgical instrument 102. The bone fastener 103 includes a head portion that defines an implant cavity and a penetrating portion configured for penetrating tissue.

The bone fastener 103 may be coated with an osteoconductive material such as hydroxyapatite and/or osteoinductive agent such as a bone morphogenic protein for enhanced bony fixation. Bone fastener 103 can be made of radiolucent materials such as polymers. Radiomarkers may be included for identification under x-ray, fluoroscopy, CT, or other imaging techniques. Metallic or ceramic radiomarkers, such as tantalum beads, tantalum pins, titanium pins, titanium endcaps, and platinum wires can be used.

The second auxiliary tool fastening mechanism 160 will be described in more detail in relation to FIGS. 8A, 8B, and 9-11. The modular surgical instrument 102 may include a tower 105 having an upper or first end 107 and a lower or second end 108. The second auxiliary tool fastening mechanism 160 is intended to be selectively installed to the first end 107 as needed, as will become evident based on the description provided in FIGS. 9-11.

The system 100 may include a polyaxial head 118 that is configured to be removably affixed to the second end 108 of the tower 105. The implant cavity 106 is configured to receive the bone fastener 103 such that the bone fastener 103 is passed to the polyaxial head 118 and screwed into a subject's spine. The implant cavity 106 extends along the length of the tower 105.

Figure 3:
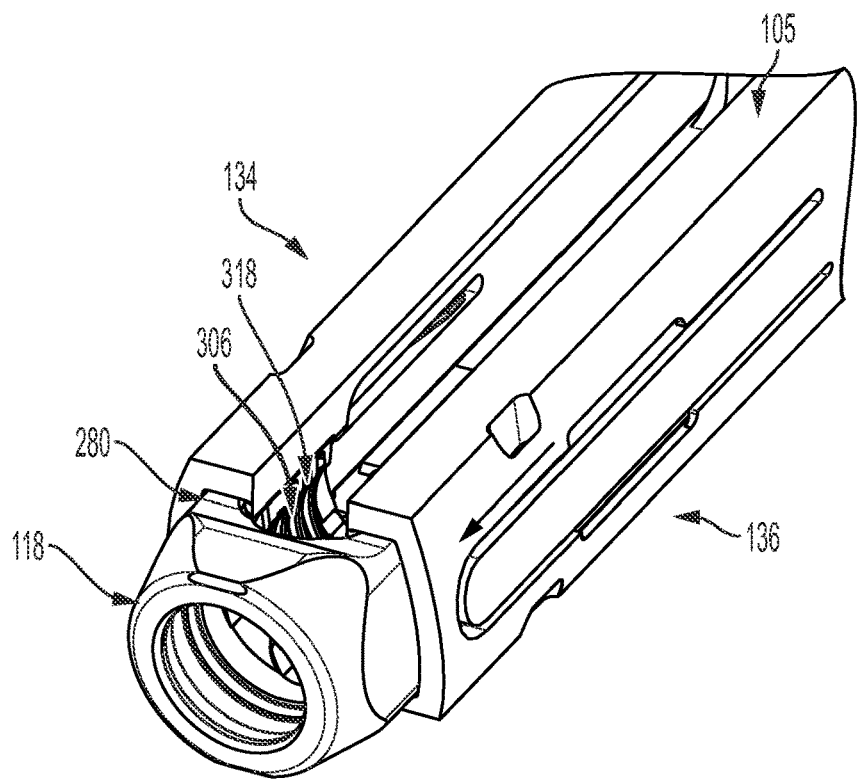
FIG. 3 is a perspective view that illustrates a lower end portion of a tower of modular surgical instrument of FIG. 2 with a polyaxial head connected.

The lower end of the tower will also be described with reference to FIGS. 2-3. FIG. 2 is a perspective view of a lower end portion of a tower 105 of modular surgical instrument 102 of FIG. 1A. FIG. 3 is a perspective view of a lower end portion of a tower of modular surgical instrument of FIG. 2 with a polyaxial head connected. The tower 105 may include a first arm 134 and a second arm 136 that are essentially the same. The modular surgical instrument 102 may include a modular surgical instrument 102 and a reducer 138. The arms 134 and 136 of the instrument 102 may be configured, for example, as described in U.S. Pat. No. 9,220,539, which is incorporated herein by reference as if set forth in full below.

Each arm defines a main arm section 237 having first and second longitudinal sides. The first longitudinal side may include a first extension 238 depending from the main arm section 237. The second longitudinal side may include a second extension 240 depending from the main arm section 237. The main arm section 237 and the depending first extension 238 and second extension 240 form a generally C-shaped arm profile. The first arm 134 and second arm 136 may be configured to be diametrically opposing so that the hollow space therebetween forms the implant cavity 106. The main arm section 237 may include a concave interior surface and a convex exterior surface. In operation, an implant can be advanced distally through the implant cavity 106. The first extension 238 of both the first arm 134 and the second arm 136 may include a planar side surface 250 extending along the length of the first extension 238.

The first and second arms 134 and 136 may include a head cavity 280 for attachment of the polyaxial head 118. The head cavity 280 may include opposing channels or rails 278 and 279. The channel or rail 278 is formed between the main arm section 237 and the depending first extension 238. The channel or rail 279 is formed between the main arm section 237 and the second extension 240.

The polyaxial head 118 in various embodiments may be affixed and locked in the head cavity 280 prior to inserting the modular surgical instrument 102 through an incision of a patient. The head cavity 280 is defined by the side-by-side seat portions 277. The C-shaped profile generally clamps around the lateral sides 318 of the polyaxial head 118, as best seen in FIG. 3. The lateral sides 318 of the polyaxial head form an implant cavity 306 therebetween, which is an extension of the implant cavity 106 of the tower 105. A longitudinal axis of the implant cavity 306 in the head 118 is aligned with the longitudinal axis of the implant cavity 106 when the head 118 is installed in the head cavity 280.

Figure 9:
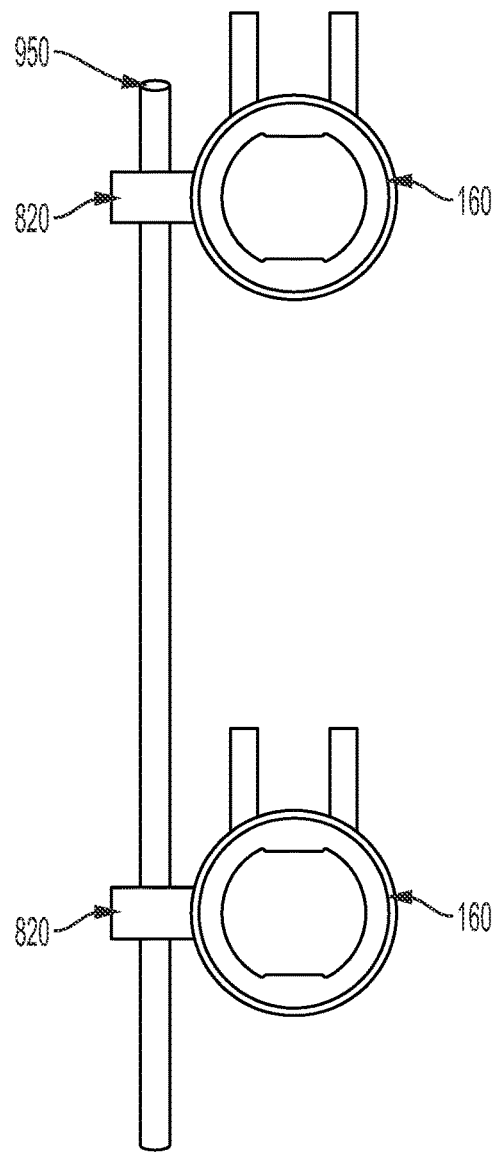
FIG. 9 is a top view that illustrates a set of auxiliary tool fastening mechanisms linked together with an elongated member.
Figure 10:
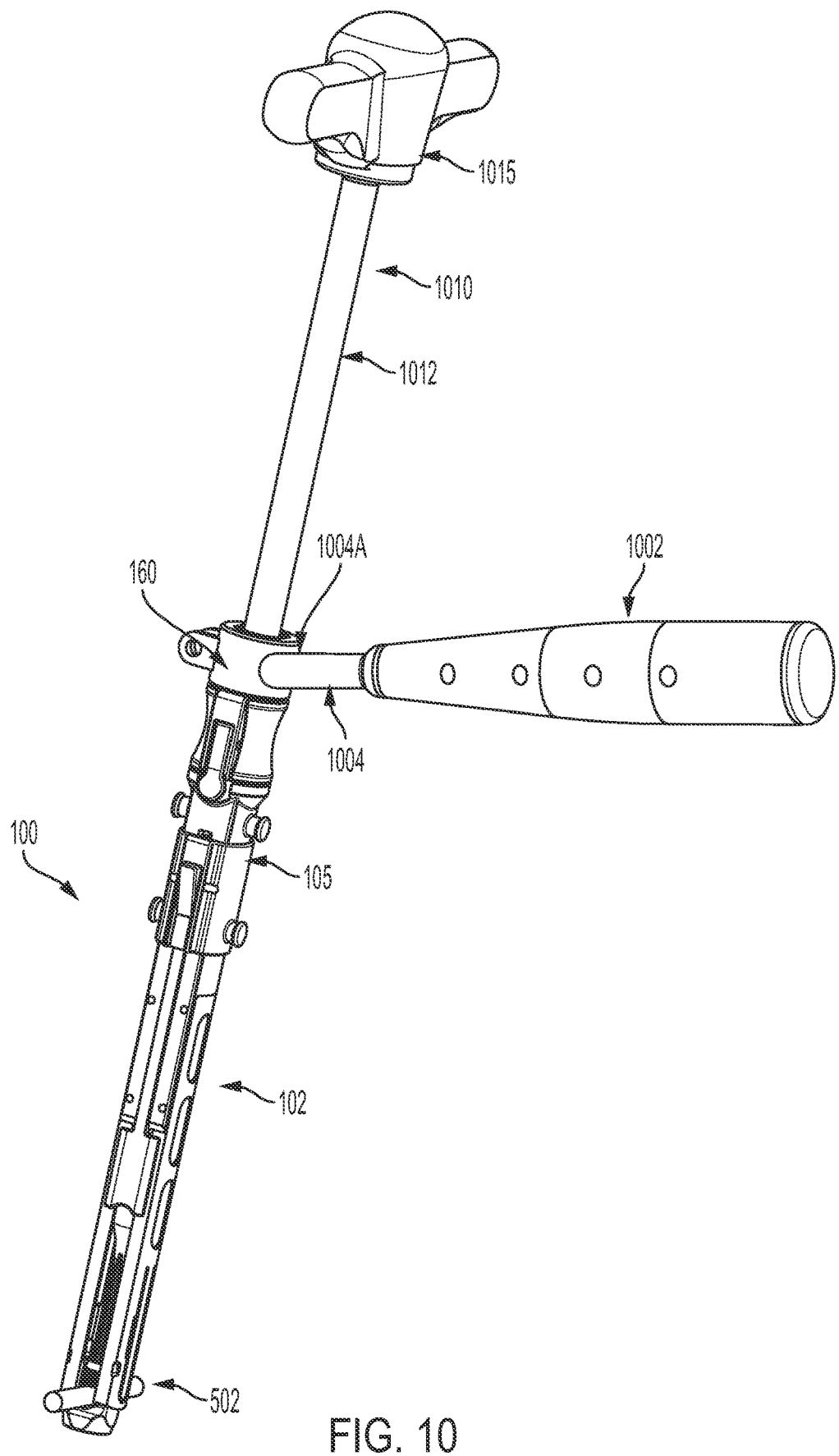
FIG. 10 is a perspective view that illustrates the modular surgical implant system with auxiliary tools fastened to the instrument.
Figure 11:
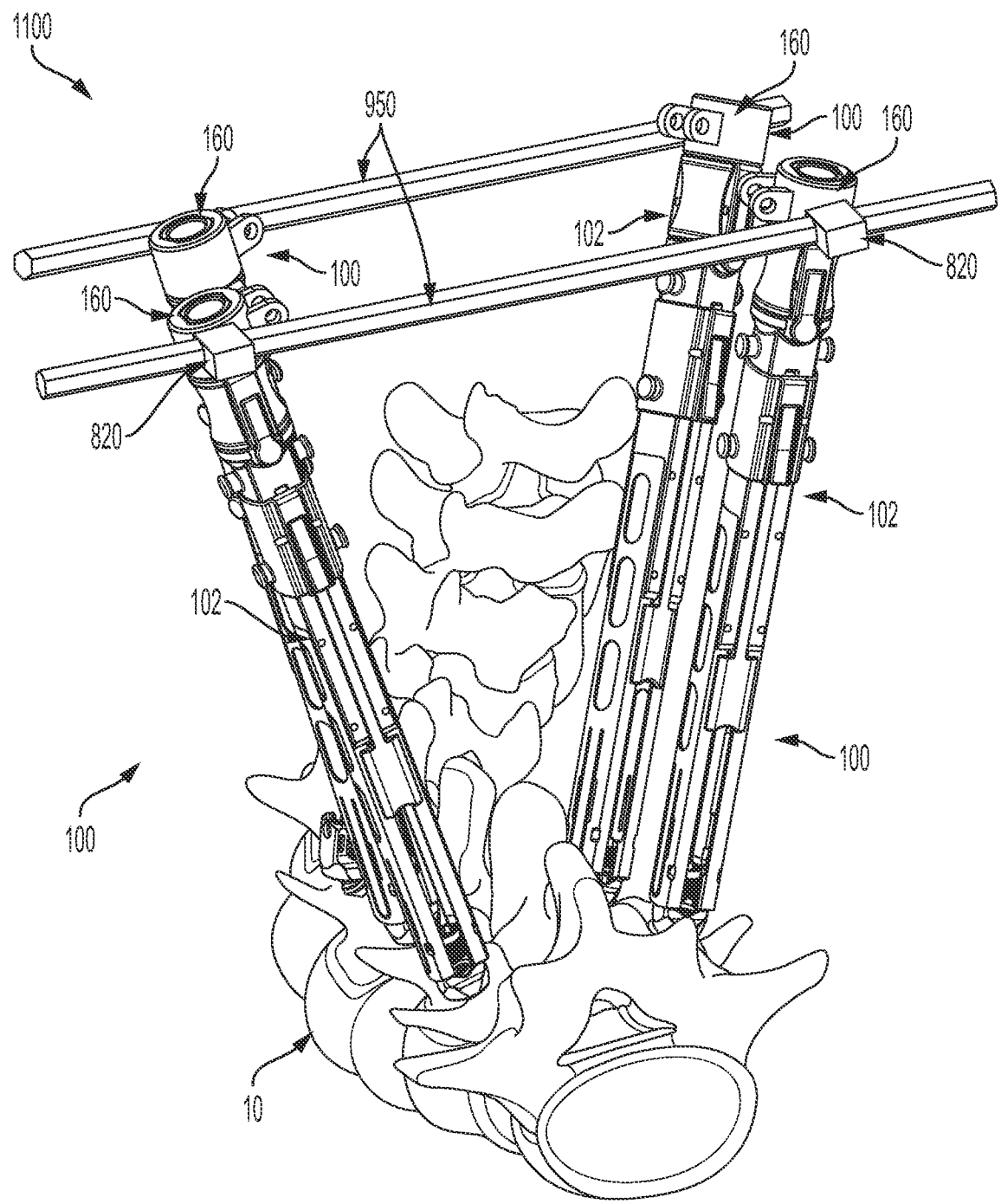
FIG. 11 is a perspective view that illustrates a set of modular surgical implant systems and a set of second auxiliary tool fastening mechanisms.

With specific reference again to FIG. 1A, the first or upper end 107 of the tower 105 may include a handle interface 110 may have a length that permits for attachment of the second auxiliary tool fastening mechanism 160, as shown in FIGS. 9-11. The system 100 may include a locking mechanism 120 having a locking lever 122, as will be described in more detail in relation to FIGS. 4A-4B. The locking mechanism 120 is configured to be received on the handle interface 110 and locked into place via locking pins 407 (FIG. 4B). FIG. 1A illustrates the locking mechanism 120 with the handle interface 110 received in the hollow center of mechanism 120 and in a locked position on the handle interface 110.

FIG. 1B is a perspective view of the modular surgical instrument 102 of FIG. 1A with the locking mechanism 120 in an unlocked position. The locking mechanism 120 is removably coupled to the tower 105 by unlocking the locking pins and sliding the locking mechanism 120 off of the handle interface 110.

The locking mechanism 120 may be configured to assist in connecting the instrument to the screw head. The locking mechanism 120 further may be configured to provide resistance to reduce the likelihood that the instrument may be inadvertently disengaged from the screw head. The ratchet mechanism may be held in place, or soft locked, by ratchet reduction mechanism 124.

The handle interface 110 is configured to receive one or more modular elements along its longitudinal axis. The one or more modular elements, such as the locking mechanism 120 and the auxiliary tool fastening mechanism 160 may be received and stacked in series along the longitudinal axis. The handle interface 110 is generally tubular shaped. The handle interface 110 may include an annular groove 112 formed in proximity to a top edge of the tower 105. The handle interface 110 may include a flat surface portion 111 formed linearly along in the tubular shape of the handle interface 110 to limit rotation of the locking mechanism 120 and/or the second auxiliary tool fastening mechanism 160 mounted to the handle interface 110.

Figure 6A:
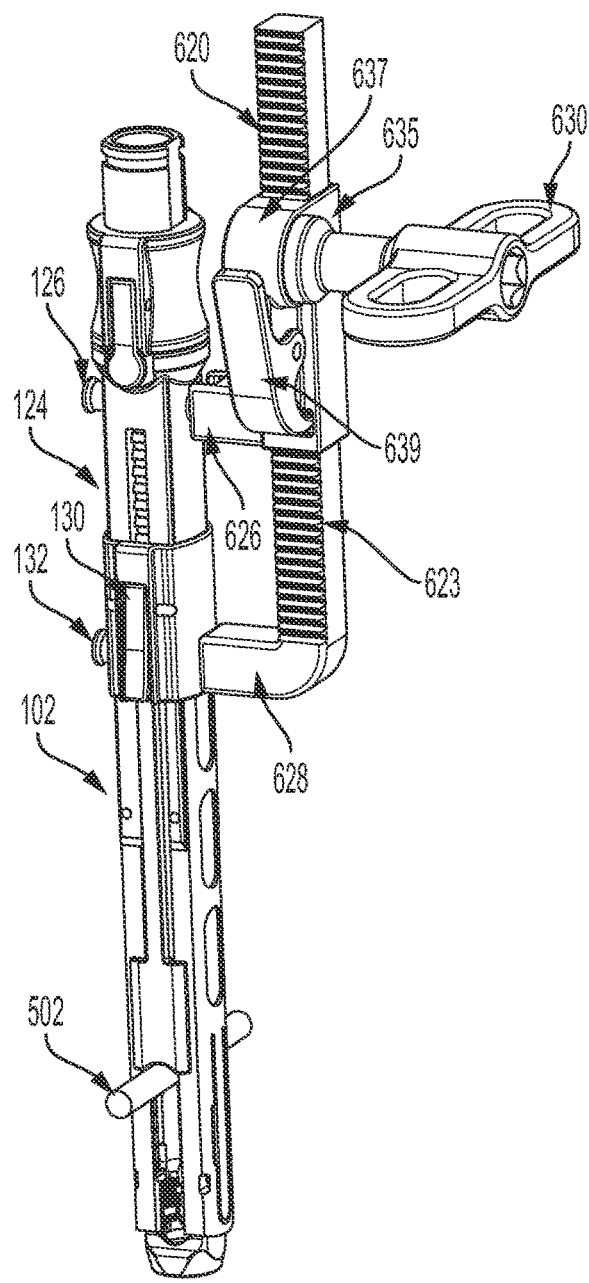
FIG. 6A is a perspective view that illustrates the instrument of FIG. 5B with an auxiliary tool connected to the ratchet reduction mechanism to lower the reducer.
Figure 6B:
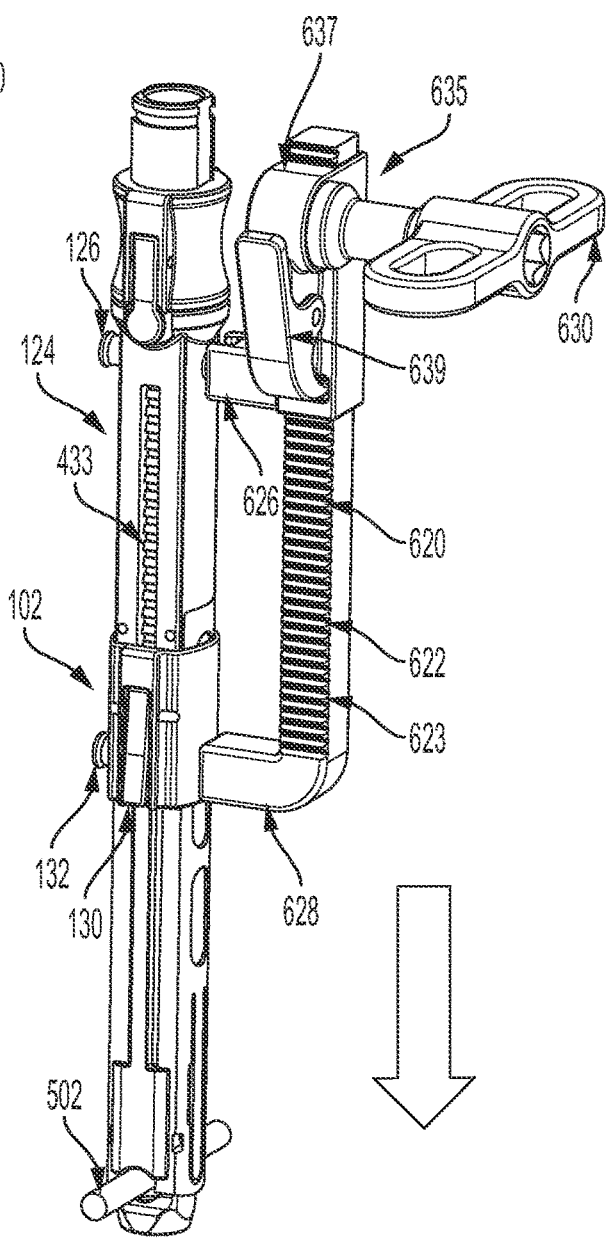
FIG. 6B is a perspective view that illustrates the instrument of FIG. 5C with the auxiliary tool connected to the ratchet reduction mechanism to lower the reducer.

The system 100 may include ratchet reduction mechanism 124 configured to interface with an integrated reducer 138. The ratchet reduction mechanism 124 may include an upper section 125 with at least one connection interface 126 for attachment of an auxiliary tool, as best seen in FIGS. 6A-6B. The ratchet reduction mechanism 124 may include diametrically opposing connection interfaces 126 each of which is on a lateral side of the tower 105 so that an auxiliary tool may be attached to a respective one lateral side of the tower 105. This may accommodate for the dexterity of the surgeon and comfort of use of the instrument 102. The reducer 138 may generally be located on the exterior side of the tower so that tools that are to be received in implant cavity 106 have a clear and unobstructed path to the polyaxial head 118. Therefore, even if the reducer is deployed, another tool can also be received in the implant cavity 106 of the tower and perform its own function during surgery.

The upper section 125 may include an upper edge that is dimensioned to form annular rib 113. The annular rib 113 may include a recess area 114 that is configured to receive a portion of locking lever 122 when the locking mechanism 120 is in a locked position, as best seen in FIG. 1A.

The ratchet reduction mechanism 124 may include ratchet collar 128 coupled to the ratchet lever or pawl 130. The ratchet collar 128 may include at least one connection interface 132. The ratchet collar 128 may include diametrically opposing connection interfaces 132. It should be understood that connection interfaces 126 and 132 may be male interfaces or other connectors. The connection interfaces 126 and 132 provide connectors for connecting an auxiliary tool 620 (FIGS. 6A-6B) to the modular surgical instrument 102. The ratchet collar 128 may be configured to slide along the first and second arms 134 and 136 by application of a force by the auxiliary tool 620 (FIGS. 6A-6B).

Figure 7A:
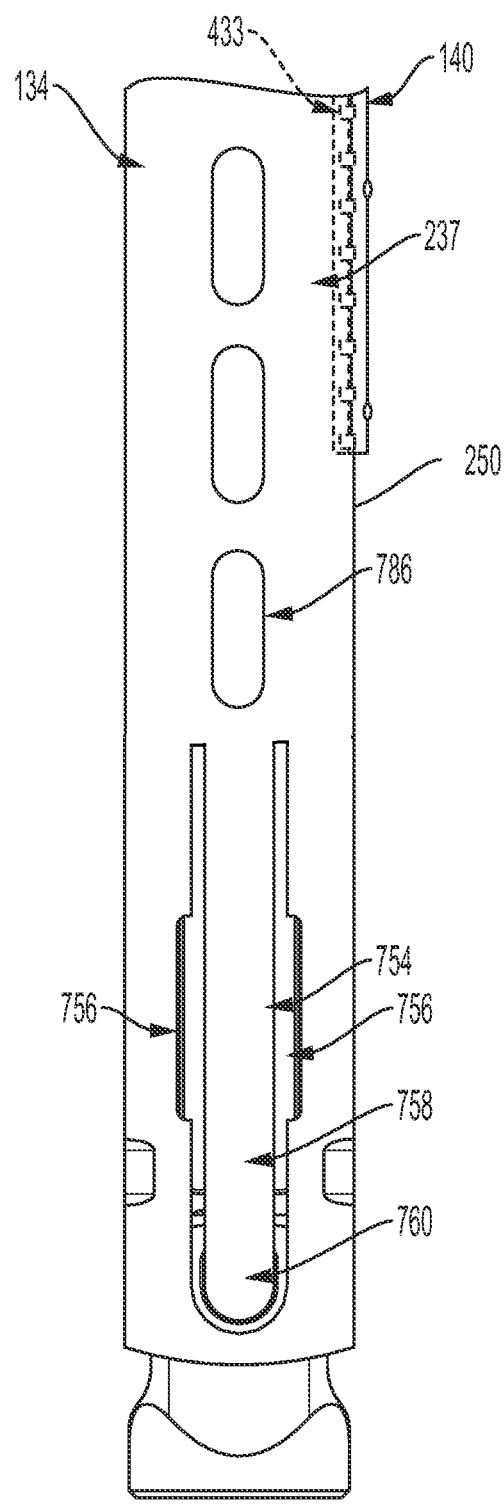
FIG. 7A is a partial side view that illustrates an arm of the tower with the reducer rail and ratchet rack shown.
Figure 7B:
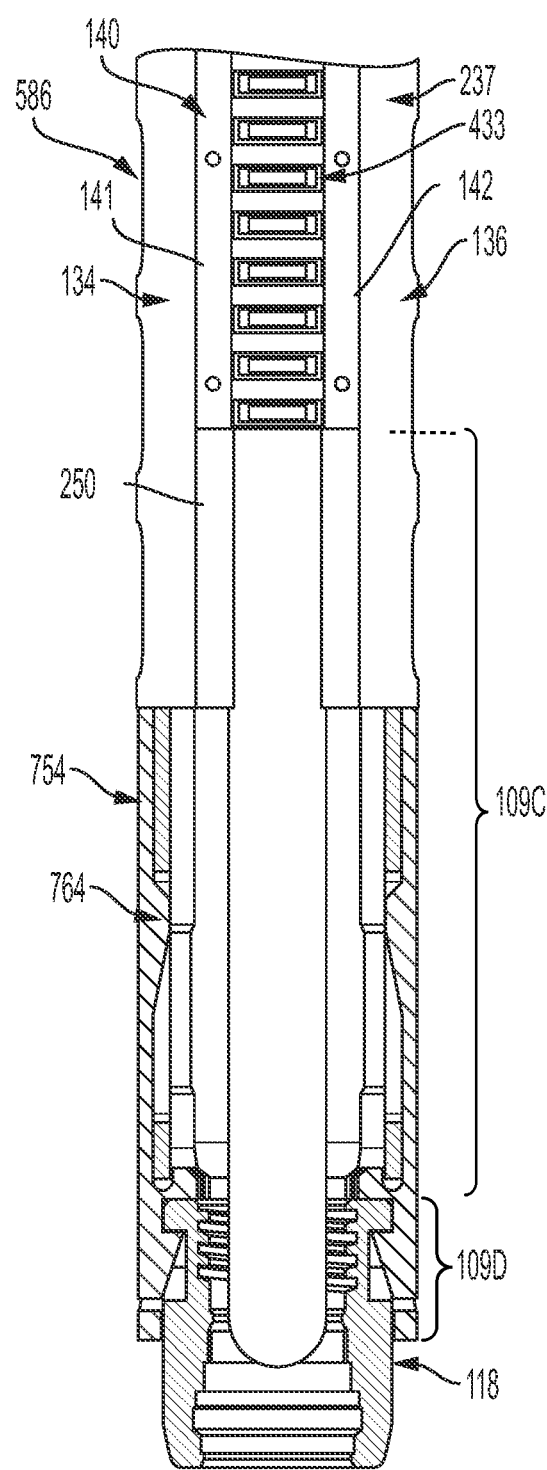
FIG. 7B is a partial front view that illustrates the arms of the tower with the reducer rail and ratchet rack shown.

The ratchet reduction mechanism 124 may include a ratchet rail 140. The ratchet rail 140 includes tracks 141 and 142, which may be generally parallel to the planar side surfaces 250 (FIGS. 2 and 7A-7B). The ratchet collar 128 is interfaced with the rail 140 to slide along the tracks 141 and 142 under a force. The ratchet reduction mechanism 124 may include a linear ratchet rack 433 (FIGS. 4A-4B) positionable between the first and second arms 134 and 136.

The system 100 may include a reducer 138 connected to the ratchet collar 128. In operation, as the ratchet collar 128 is slid in the direction toward the second end 108 by the ratcheting action between pawl 130 and the linear ratchet rack 433 under application of a force. As the ratchet collar 128 slides downward, the reducer 138 follows in unison. A portion of the reducer 138 is generally parallel and adjacent to the ratchet rail 140 when the reducer is in at least one position.

Figures 5A, 5B, 5C:
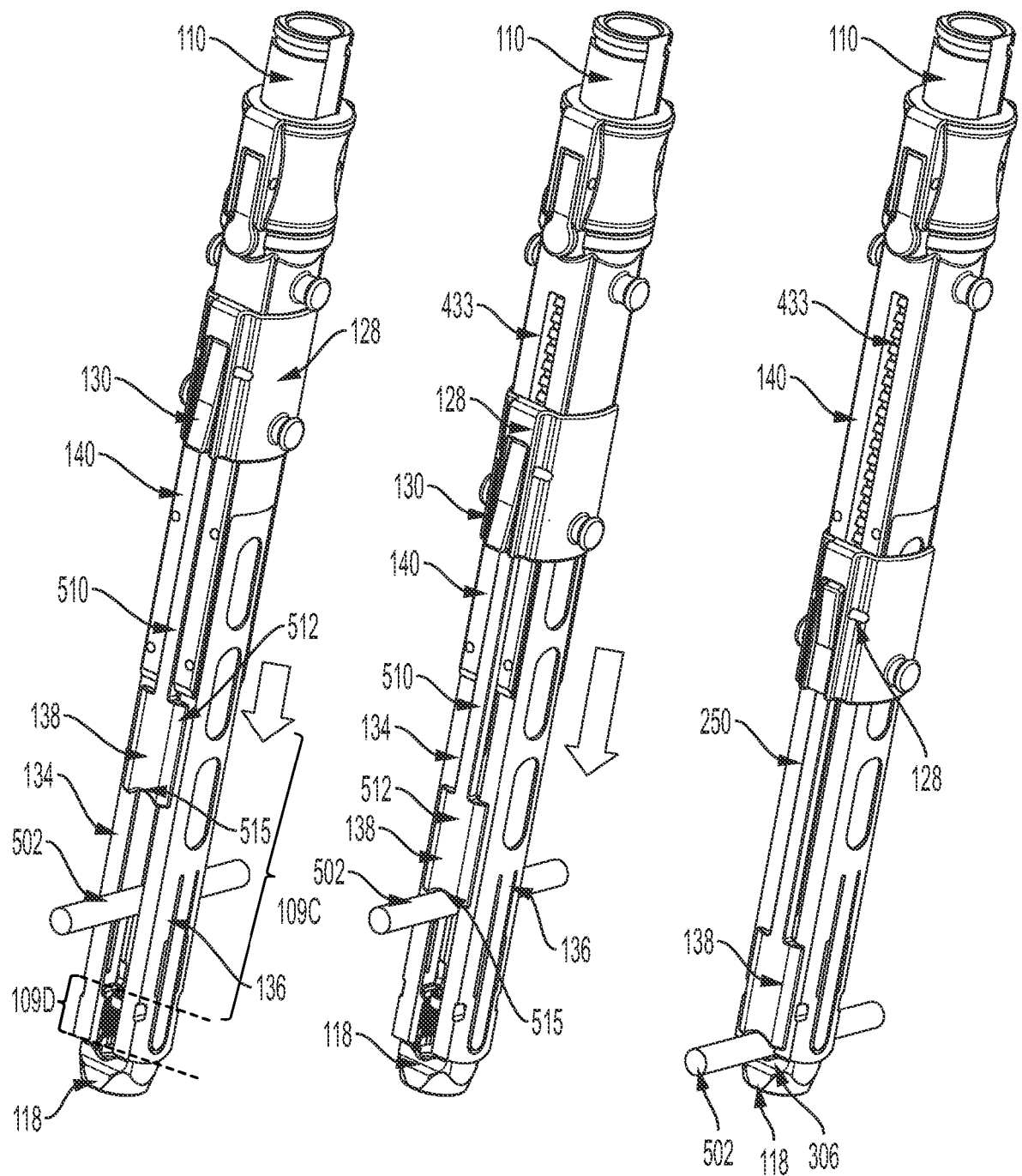
FIG. 5A is a perspective view that illustrates the modular surgical instrument with a rod installed between arms of the tower and a reducer in a first position.
FIG. 5B is a perspective view that illustrates the modular surgical instrument with the rod installed between arms of the tower and the reducer in a second position.
FIG. 5C is a perspective view that illustrates components of a modular surgical instrument with the rod in a lower position between arms of the tower and the reducer in a third position.

For illustrative purposes and to assist in describing the tower 105, the tower 105 is described in sections. The tower 105 may include tower segments 109A (FIG. 4B), 109B (FIG. 4B), 109C (FIGS. 5A and 7B), and 109D (FIGS. 2, 5A and 7B). The tower segments, collectively, form an implant cavity 106 and extend from the first end 107 to the second end 108. The tower segment 109A form a tubular body for the handle interface 110. The tower segment 109A may sometimes be referred to as a handle segment. The tower segments 109C and 109D may include both a first arm 134 and a second arm 136, which may be coupled and arranged to be diametrically opposing to from a portion of the implant cavity 106. The tower segment 109B corresponds to the region for integration and installation of components of the ratchet reduction mechanism 124. The tower segment 109C is below the rail 140 and may be configured to receive various surgical tools (i.e., rod 502 of FIGS. 5A-5C) between parallel arms 134 and 136 and/or other accessories at locations below the reducer 138. The tower segment 109B may sometimes be referred to as a ratchet segment. The tower segments 109D includes an interface for the connection or attachment of the polyaxial head 118 to the second end 108.

A configuration of the handle interface 110, locking mechanism 120, and the ratchet reduction mechanism 124 is best seen in FIGS. 4A-4C. Specifically, FIG. 4A illustrates a partial cross-sectional view along cross section 4A-4A of an upper end portion of a tower 105 of modular surgical instrument 102 of FIG. 1A. FIG. 4B illustrates a partial cross-sectional view along cross section 4B-4B of an upper end portion of a tower 105 of modular surgical instrument 102 of FIG. 1A. FIG. 4C illustrates a partial cross-sectional view along cross section 4C-4C of an upper end portion of a tower 105 of modular surgical instrument 102 of FIG. 1A.

As can be seen in FIGS. 4A and 4B, the tower segments 109A and 109B form a unitary tower body portion to form the handle interface 110. The ratchet reduction mechanism 124 is integrated into the arms 134 and 136. As best seen in FIG. 4B, the handle interface 110 may include opposing flat surface portions 111. The integrated portion links the arms 134 and 136 together at an upper end of the arms. However, the lower end of the arms remain separated. As shown in FIGS. 4A and 4B, the handle interface 110 may form a generally tubular body. However, a portion of the tower segment 109C includes the diametrically opposing arms 134 and 136, as best seen in FIG. 7B.

Returning again to FIGS. 4A-4B, locking mechanism 120 may include a locking collar 422 with a locking lever 122 hingedly coupled to the collar 422. The locking lever 122 may be a rocking lever 122. The collar 422 may include a lever cavity 423 for recessing a portion of the lever 122. The lever 122 may be hingedly coupled in the lever cavity 423 via pin 426. The lever 122 may include a top lever section 427 configured to be recessed in the lever cavity 423 when engaged. The lever 122 includes a bottom lever section 428, which is moved toward the tower 105 when lever 122 is disengaged. In various embodiments, the locking mechanism 120 may include diametrically opposing rocking levers 122. The interior of the collar 422 may be fitted with flat interior surfaces to mate with flat surface portions 111.

The collar 422 may include locking channels 430 configured to receive a locking pin 407 coupled to the tower 105. In various embodiments, the collar 422 may include diametrically opposing locking channels 430; and the tower 105 may include diametrically opposing pins 407, which may be configured to be aligned with the locking channels 430 when the collar 422 is in position to be locked. The pins 407 when received in the locking channels 430 fasten the collar 422 into position. The pins 407 may be spring biased coupled, which is not shown in the illustration.

The outer surface of the handle interface 110 may include diametrically opposing locking notches 410. In operation, as the locking collar 422 is slid along the handle interface 110, the top lever section 427 may slid along exterior the surface of handle interface 110. When the locking collar 422 is in position to be locked, the top lever section 427 of the levers 122 may pivot into the locking notches 410 and lock therein so that the locking collar 422 cannot be moved upward along the handle interface 110 until the levers 122 moved from their locked position by pressing on bottom lever section 428. Pressing on the bottom lever section 428 causes the top lever section 427 to move out of the locking notch 410. The top lever section 427 is spring biased by spring 440. The diametrically opposing configuration, may allow the bottom lever section 428 to be pressed simultaneously, so that the top lever sections 427 may be unlocked from notches 410 simultaneously.

The ratchet reduction mechanism 124 with a ratchet lever or pawl 130 will be described in more detail in relation to FIGS. 4A-4C. The ratchet reduction mechanism 124 may include ratchet collar 128 with a ratchet lever cavity 450 for recessing a portion of the ratchet lever or pawl 130. The ratchet lever or pawl 130 may be hingedly coupled in the ratchet lever cavity 450 via pin 436. The ratchet lever or pawl 130 may include a top section 435 configured to be recessed in the ratchet lever cavity 450 when engaged with the ratchet rack 433. The top section 435 is spring biased via spring 442. The ratchet lever or pawl 130 includes a bottom section 432, which moved toward the tower 105 when the ratchet lever or pawl 130 is disengaged from the ratchet rack 433. In various embodiments, the ratchet reduction mechanism 124 may include diametrically opposing ratchet lever or pawl 130, which operate in unison. The ratchet rack 433 may include a plurality of ramp elements 470, which the lever or pawl 130 will follow a ramp surface of the ramp elements 470 to an end and pivot to start the next ramp element 470. There is a gap 471 between ramp elements 470.

The operation of the reducer 138 will now be described.

FIG. 5A is a perspective view of the modular surgical instrument 102 with a rod 502 installed between arms 134 and 136 of the tower 105 and a reducer 138 in a first position. The system 100 may include the rod 502, which can be used to link one or more pedicle screws together. The rod 502 is shown generally perpendicular to the implant cavity 106. The rod 502 has a diameter configured to be inserted between the gap between the parallel arms 134 and 136. FIG. 5B is a perspective view of the modular surgical instrument 102 with the rod 502 installed between arms 134 and 136 and the reducer 138 in a second position. This sliding motion of the ratchet collar 128 is configured to move the integrated reducer 138 in a direction toward the second end of the tower 105.

The reducer 138 includes a reducer arm 510 and a reducer cradle 512. The reducer arm 510 is an elongated planar member, which is configured to fit between the tracks 141 and 142. The reducer cradle 512 may include a seat 515 for placement of the elongated member or rod 502. A bottom edge of the cradle 512 has a generally concave profile to form the seat 515. In operation, as the reducer 138 is slid toward the second end 108 of the tower, the reducer 138 engages a top side of the rod 502 and applies a force thereto.

FIG. 5C is a perspective view of the modular surgical instrument 102 with the reducer 138 in a third position, which corresponds to being positioned in the implant cavity 306 (FIG. 3) of the polyaxial head 118. As the reducer 138 is slid toward the second end 108, the reducer 138 is configured to apply a force to rod 502 extending between the first and second arms 134 and 136. The force applied to rod 502 moves the rod 502 into the polyaxial head 118. In operation, the reducer cradle 512 include planar member, which has a width, which is greater than the width of the gap between the arms 134 and 136. The reducer cradle 512 is configured to extend between the first and second arms 134 and 136 and slide above and parallel to the planar side surfaces 250.

In operation, the rod 502 may be positioned between the first and second arms 134 and 136 and may be linked to two or more modular surgical instrument 102 simultaneously, by sliding the rod in the gap between the arms 134 and 136, in various embodiments.

FIG. 6A illustrates the perspective view of the instrument of FIG. 5B with an auxiliary tool 620 connected to the ratchet reduction mechanism 124 to lower the reducer 138. In some embodiments, the system 100 may include auxiliary tool 630. FIG. 6B illustrates the perspective view of the instrument of FIG. 5C with the auxiliary tool 620 connected to the ratchet reduction mechanism to lower the reducer 138. The auxiliary tool 620 may be used to apply a force to the ratchet collar 128. As the force is applied to the ratchet collar 128, the pawl 130 moves downward along the ratchet rack 433, as described above. The auxiliary tool 620 may include a first linear support 622 and a pair of depending supports 626 and 628. The pair of supports 626 and 628 may be generally perpendicular to the linear support 622 that include a linear gear 623. The pair of supports 626 and 628 may be arranged in a spaced relationship with respect to each other. The space relation is adjusted as the tool 620 moves the ratchet collar 128 downward. As can be seen in FIG. 6A, the pair of supports 626 and 628 has a first distance between each other. As can be seen in FIG. 6B, the pair of supports 626 and 628 has a second distance between each other. In general, the pair of supports 626 and 628 includes couplers (not shown) for connecting to the male interfaces 126 and 132, respectively. For example, support 626 may be connected to male interface 126. Then, support 628 is connected to male interface 132. The tool 620 may include a tool handle interface 635 that may be a rack and pinion assembly. The rack and pinion assembly may include a rotatory element in housing 637, such as a gear. The rack and pinion assembly may include a tool handle 630 or knob connected to the rotatory element in housing 637. In operation as the tool handle 630 or knob rotates, the rotatory element in housing 637 also rotates by action of the tool handle 630. The tool handle interface 635 includes a ratchet pawl 639. The ratchet pawl 639 ratchets in one direction and serves as a lock as it moves into engagement with the teeth of the linear gear 623. The handle 630 or knob may be rotated in a first direction to cause the tool handle interface 635 to move along the linear support 622 in an upward direction, forcing the ratchet collar 128 to move downward.

When the ratchet pawl 639 is pressed, it unlocks and allows the rack to translate freely. When the ratchet pawl 639 is un-pressed, the ratchet pawl 639 is locked. When the unlocked rack is translating, the pinon gear is still engaged, so the handle 630 or knob will spin. When the gear or rotatory element in housing 637 is turned, it translates the rack portion of the tool 620. The pinion is always engaged with the rack.

Additional details of the tower 105 will be described in relation to FIGS. 7A-7B. FIG. 7A illustrates a partial side view of an arm of the tower with the reducer rail 140 and ratchet rack 433 shown. FIG. 7B illustrates a partial front view of the arms 134 and 136 of the tower with the reducer rail 140 and ratchet rack 433 shown. As best seen in FIGS. 7A-7B, the tower may include projection 754 that may include planar side surfaces 756 and a first locking element 758 at a distal end of projection 754 extending between side surfaces 756. First locking element 758 has a tip 760.

The projection 754 on an interior side of the projection 754 a ramp 764 is integrated into the surface profile. Ramp 764 is substantially planar and has a width that is less than a width of projection 754.

Figure 8A:
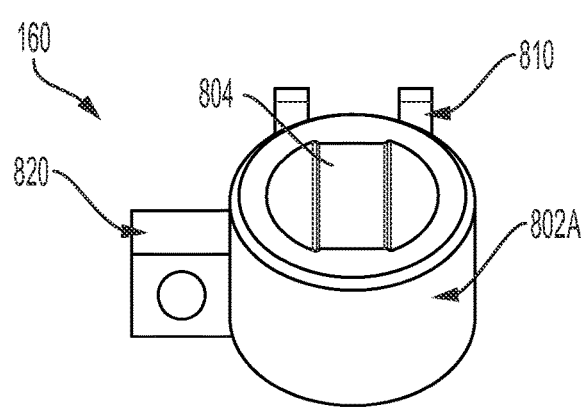
FIG. 8A is a perspective view that illustrates a second auxiliary tool fastening mechanism.

FIG. 8A illustrates a second auxiliary tool fastening mechanism 160. FIG. 9 illustrates a set of auxiliary tool fastening mechanisms 160 linked together with an elongated member or rod 950. The rod 950 may be a derotation link. The second auxiliary tool fastening mechanism 160 may include a generally cylindrical structure 802A with a hollow center. The interior surface of the structure 802A may include a rib 804 for engaging the annular groove 112 (FIG. 1A). The interior surface of structure 802A may also include flat surface portions to mate with flat surface portions 111. The second auxiliary tool fastening mechanism 160 may include first connector 810 and a second connector 820. The first connector 810 may be used to connect another elongated member or rod 950 to the instrument 102. The fastening mechanism 160 may have a lever that snaps into the groove 112. For example, a lever similar to lever or pawl 130 may be incorporated into the fastening mechanism 160. A lever may be used to connect the counter-torque and the derotation linkage, for example.

FIG. 11 illustrates a perspective view of a set 1000 of implant systems 100 and a set of second auxiliary tool fastening mechanisms 160 (FIG. 8A). The two of the systems 100 of the set 1000 is shown interconnected by rod 950. Another pair of systems 100 of set 100 is shown interconnected by a second rod 950. It should be understood that the set 1000 of systems 100 may have one or more systems 100. This arrangement may be used, for example, for derotation of the various vertebra or vertebral segments. Additional interconnections between towers may further be provided for derotation of additional segments across and/or along the spine as, for example, those interconnections are disclosed and manipulated in U.S. Pat. No. 7,655,008 and/or U.S. Patent Application Publication 2013/0211453, which are both incorporated by reference in their entirety.

Figure 8B:
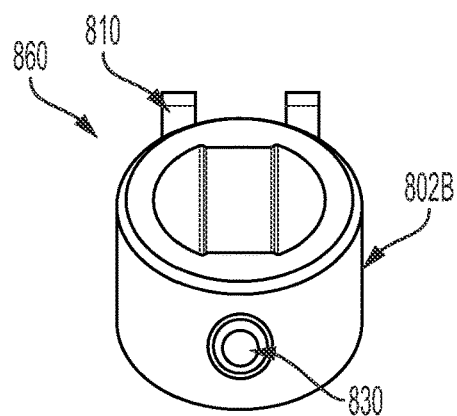
FIG. 8B is a perspective view that illustrates another second auxiliary tool fastening mechanism.

FIG. 8B illustrates another second auxiliary tool fastening mechanism 860. The tool fastening mechanism 860 is similar to the tool fastening mechanism 160. Therefore, only the differences will be described in detail. In FIG. 8B, the cylindrical structure 802B includes a tool connector 830. The tool connector 830 may be a female connector or a threaded aperture. It should be understood, the connector is for illustrative purposes and may include other type of fasteners, such as male interfaces, snap-on connectors, friction fit connectors, etc.

FIG. 10 illustrates a perspective view of components of the modular surgical implant system 100 with auxiliary tools fastened to the instrument 102. The auxiliary tools include a driver 1010 with an elongated rod 1012 having a longitudinal axis, which when moved or slid in the implant cavity 106 is parallel to the longitudinal axis of tower 105. The upper end of the rod 1012 has a driver handle 1015 affixed thereto for rotating the rod and apply a torque to the pedicle screw. The second auxiliary tool fastening mechanisms 860 is shown attached to the handle interface 110. The second auxiliary tool fastening mechanisms 860 has an auxiliary handle device 1002 coupled thereto for use by surgeons or other operating room staff to assist in applying a resistance torque to the tower 105. The resistance torque may prevent undue stresses to the implant or spine when applying a break-off torque with the driver 1010. The auxiliary handle device 1002 include a shaft 1004 and a connector 1004A at the end of the shaft to connect to tool connector 830 (FIG. 8B).

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A modular surgical instrument comprising:
   a tower having a first end, a second end and a ratchet segment between the first end and the second end;
   a ratchet reduction mechanism including:
      a ratchet lever,
      a linear ratchet rack integrated into the ratchet segment of the tower at a location between the first end and the second end,
      a ratchet collar coupled to the ratchet lever and configured to slide along the ratchet segment by application of an applied force, and
      a ratchet rail comprising parallel tracks to which the ratchet collar is interfaced; and
   a reducer affixed to the ratchet reduction mechanism, configured to move in unison with the slide of the ratchet collar, and comprising
      a reducer arm that is configured to fit between the parallel tracks, and
      a reducer cradle positioned at a lower end of the reducer arm;
   wherein the reducer is configured to apply pressure to move a rod when coupled to the tower downward toward the second end of the tower.

2. The modular surgical instrument of claim 1, wherein the tower further comprises a handle segment, the handle segment includes a handle interface coupled to the first end of the tower above the ratchet segment.

3. The modular surgical instrument of claim 2, wherein the handle interface comprises:
   a tubular shape;

an annular groove formed in a top end of the tubular shape; and a flat surface portion formed in the tubular shape to limit rotation of a tool coupler mounted to the handle interface.

4. The modular surgical instrument of claim 3, further comprising a locking mechanism that is configured to be slid on and locked to the handle interface, wherein a locking lever is configured to lock the ratchet collar in a first mode and unlock the ratchet collar in a second mode.

5. The modular surgical instrument of claim 1, wherein:

the ratchet segment comprises a first connection interface; and the ratchet collar comprises a second connection interface, wherein the first connection interface and the second connection interface are configured to affix an auxiliary tool to the ratchet reduction mechanism for generating the applied force.

6. The modular surgical instrument of claim 1, wherein the tower includes a head cavity at the second end for attachment of a polyaxial head.

7. A surgical implant system comprising:

a polyaxial head; and a modular surgical instrument comprising:

a tower having a first end, a second end and a ratchet segment between the first end and the second end, a ratchet reduction mechanism including a ratchet collar interfaced with the ratchet segment and a ratchet rail comprising parallel tracks to which the ratchet collar is interfaced, and a reducer affixed to the ratchet reduction mechanism, configured to move in unison with sliding motion of the ratchet collar toward the polyaxial head, and comprising a reducer arm that is configured to fit between the parallel tracks, and a reducer cradle positioned at a lower end of the reducer arm;

wherein the reducer is configured to apply pressure to move a rod when coupled to the tower downward toward the second end of the tower.

8. The system of claim 7, wherein the tower further comprises a handle segment, the handle segment includes a handle interface coupled to the first end of the tower above the ratchet segment.

9. The system of claim 8, wherein the handle interface comprises:

a tubular shape;

an annular groove formed in a top end of the tubular shape; and a flat surface portion formed in the tubular shape to limit rotation of a tool coupler mounted to the handle interface.

10. The system of claim 9, wherein the instrument further comprises a locking mechanism that is configured to be slid on and locked to the handle interface, wherein a locking lever is configured to lock the ratchet collar in a first mode and unlock the ratchet collar in a second mode.

11. The system of claim 8, further comprising:

at least one auxiliary tool fastening mechanism is configured to be received on the handle interface above a locking mechanism, each auxiliary tool fastening mechanism is configured to affix at least one of an accessory or auxiliary tool to the tower.

12. The system of claim 11, further comprising:

the at least one accessory; and a set of auxiliary tools, wherein the at least one auxiliary tool fastening mechanism is configured to connect simultaneously two tools of the set of auxiliary tools.

13. The system of claim 7, wherein the ratchet reduction mechanism further comprises:

a ratchet lever; and a linear ratchet rack integrated into the ratchet segment of the tower at a location between the first end and the second end;

wherein the ratchet lever is pivotally coupled to the ratchet collar and the ratchet collar is configured to slide along the ratchet segment by application of an applied force.

14. The system of claim 7, wherein:

the ratchet segment comprises a first connection interface; and the ratchet collar comprises a second connection interface, wherein the first connection interface and the second connection interface are configured to affix an auxiliary tool to the ratchet reduction mechanism for generating a force.

15. The system of claim 7, further comprising an elongated rod, wherein the tower comprises parallel arms having a longitudinal axis and a gap between the arms to receive the rod between the arms such that the rod is perpendicular to the longitudinal axis at a location below the reducer.

16. The system of claim 15, wherein the reducer is configured to push the rod between the arms and down into a cavity of the polyaxial head.

17. The system of claim 7, further comprising:

at least one accessory including a de-rotation rod;

a set of auxiliary tools;

a pedicle screw configured to be installed in the polyaxial head; and an auxiliary tool fastening mechanism that is configured to connect to the first end of the tower, wherein the auxiliary tool fastening mechanism is configured to connect the de-rotation rod and the at least one auxiliary tool to the tower.

* * * * *